(12) United States Patent
Anton

(10) Patent No.: US 6,292,955 B1
(45) Date of Patent: Sep. 25, 2001

(54) ADAPTER FOR FIXING SPECTACLE LENSES

(76) Inventor: Wolfgang Anton, Schönblickstrasse 18, D-70825 Korntal-Münchingen (DE)

(*) Notice: Subject to any disclaimer, the term of this patent is extended or adjusted under 35 U.S.C. 154(b) by 0 days.

(21) Appl. No.: 09/446,610

(22) PCT Filed: Apr. 14, 1999

(86) PCT No.: PCT/EP99/02512

§ 371 Date: Mar. 20, 2000

§ 102(e) Date: Mar. 20, 2000

(87) PCT Pub. No.: WO99/54000

PCT Pub. Date: Oct. 28, 1999

(30) Foreign Application Priority Data

Apr. 21, 1998 (DE) .......................................... 298 07 174 U

(51) Int. Cl.⁷ .................................................. A61F 9/02
(52) U.S. Cl. .................................................. 2/441; 2/434
(58) Field of Search .............................. 2/434, 441, 443, 2/431, 432, 435, 439, 428, 430; 128/857, 858; 351/158

(56) References Cited

U.S. PATENT DOCUMENTS

| 3,122,962 | * | 3/1964 | De Angelis | 2/443 |
| 3,533,686 | * | 10/1970 | O'Shea | 2/434 |
| 4,648,394 | * | 3/1987 | Wise | 128/201.24 |
| 4,971,431 | * | 11/1990 | Gerard | 351/86 |
| 5,137,341 | * | 8/1992 | Gendol et al. | 351/43 |
| 5,412,438 | * | 5/1995 | Bolle' | 351/44 |
| 5,657,106 | * | 8/1997 | Herald, Jr. et al. | 351/57 |
| 5,819,321 | * | 10/1998 | Wang | 2/428 |
| 5,890,237 | * | 4/1999 | Herman | 2/440 |

* cited by examiner

Primary Examiner—John J. Calvert
Assistant Examiner—Katherine Moran
(74) Attorney, Agent, or Firm—Kriegsman & Kriegsman

(57) ABSTRACT

The invention relates to an adapter (20) for reversibly fixing a spectacle lens (10) to the shield (30) of a pair of safety glasses (40). According to the invention, said adapter (20) has a shaped ring which consists of a transparent or opaque, permanently elastic material and which has adhesive surfaces for joining the spectacle lens (10) to the shield (30).

15 Claims, 2 Drawing Sheets

ADAPTER FOR FIXING SPECTACLE LENSES

Figure 1:
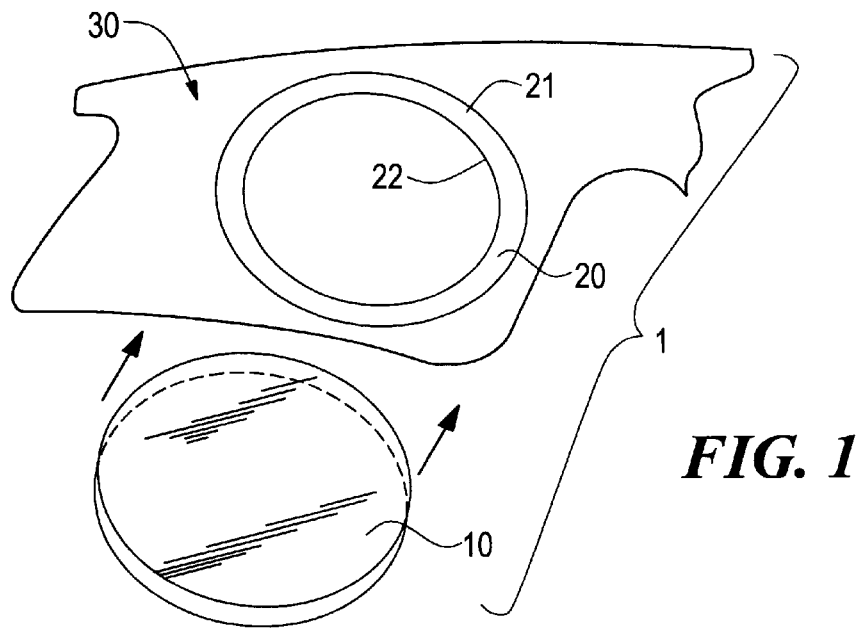

The present invention relates to an adaptor for fixing spectacle lenses according to the preamble of Claim 1.

This invention relates to a frameless joining of commercial safety glasses which have a continuous transparent shield or two separated, extremely curved transparent shields as an eye cover, in particular, sports glasses, sports sunglasses, diver's goggles and industrial safety glasses, to spectacle lenses of individual lens strengths according to the person wearing the safety glasses. People who must wear glasses have difficulty wearing current safety glasses which typically have transparent shield in the form of a continuous plate as an eye cover. These types of safety glasses, for example, are available under the trade names Oakley M-Frame Series, Bolle Edge Series and Breakaway Series, Alpina Gravity 0/Bel Air Series, Swiss Eye, etc.

Most producers offer exchangeable frame adapters that are inserted into the spectacle frame for the fitting of spectacle lenses. These systems, however, have some serious disadvantages. For example, with sports glasses, the largest distance between the safety glasses and the eyes increases considerably, which, as a rule, is about 15 mm. This reduces shielding capacity of the shield or the two shields, so that wind swirls may occur between the shield and the eye. Furthermore, in unfavorable weather conditions, the shields tend to fog up. In order to clean the shields, it is necessary to remove the adapter. Furthermore, conventional frame adapters are rather heavy.

In diver's goggles, silicate spectacle lenses have for some time been joined to the rear areas of the shield of the diver's goggles by means of hardened adhesives, such as an epoxy adhesive. This can result in a change of the chromatic dispersion. Moreover, there may be problems in which, when using the diver's goggles, the shield of the goggles has a considerably lower temperature, which is determined by the temperature of the surrounding water, than the spectacle lenses, which are heated by the warmth of the face of the goggles wearer. This difference in temperature causes the spectacle lenses to expand more than the shield. The spectacle lenses may loosen from the back due to this difference in temperature, but since the hardened adhesive is not elastic and unable to compensate for the stress caused by the varying expansion temperature, the lenses may crack.

Classical safety glasses normally consist of frames and hardened spectacle lenses provided with shielding sections. Hardened spectacle lenses, however, are very expensive and often must be replaced due to excessive wear. Other safety glasses have an inserted frame adapter, as explained above in connection with sports glasses. Safety glasses provided with this type of frame adapter have the same disadvantages as the sports glasses described above.

Another great problem, which reduces the suitability of the safety glasses provided with frame adapters, is the astigmatism of oblique bundles which occurs with curved shields as a result of the angular adjusting position of the correcting spectacle lenses. This can be avoided only if it is possible to fix the correcting spectacle lenses so that they are as vertical to the optical axis as possible, which is difficult to impossible for curved shields.

These disadvantages considerably restrict the usability and the application of these safety glasses for the wearers.

The object of the present invention is to eliminate the above described disadvantages found in conventional plug-on adapter systems and to fix the spectacle lens to the shields in a simpler, safer and more compatible manner, i.e., with increased benefit to the spectacle. Further, an excessive increase in weight, which occurs with conventional frame adapters, is to be avoided.

The solution is provided by an adapter with the features of claim 1. According to the invention, the adapter is a shaped ring of a transparent or opaque permanently elastic material, in which the shaped ring has adhesive surfaces for joining the spectacle lens to the shield. The adapter according to the invention connects the rear of the shield of a pair of safety glasses to the front of the spectacle lens tightly and immovably, but reversibly, and thus also removably. The adapter according to the invention thus is able to finction completely without seats or frames for spectacle lenses. The system, which consists of a pair of safety glasses and spectacle lens, is protected against condensation due to the hermetic seal of the space between the shield and the spectacle lens. The weight of the adapter according to the invention is only a fraction of that of a conventional frame adapter. Since the adapter is fastened reversibly and thus can be removed from the shield of the safety glasses and spectacle lens, said adapter is reusable.

Advantageous further developments result from the subordinate claims. The shaped ring may have a flat cross section or it may have the shape of an adhesive strip, preferably with a thickness ranging between 0.5 mm to 2.0 mm. Adapters of this type are suitable, for example, for flat shields such as diver's goggles. The shaped ring may have a wedge-shaped cross section. One possible structure comprises a core of transparent or opaque material that is provided with adhesive surfaces in the form of at least one layer with an adhesive material. These types of adapter are suitable for lining strong curves at the front of positive lenses. The deciding factor for the use of adapters always are the anatomical or optical requirements.

The core preferably is made of a plastic material, preferably polycarbonate or nylon. This material can be stressed mechanically and can withstand considerable temperature fluctuations without becoming porous.

Figure 2A:
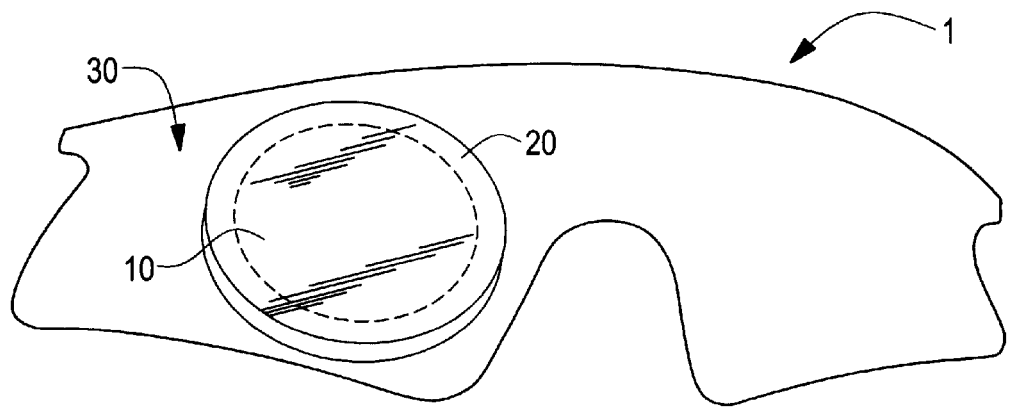
Figure 2B:
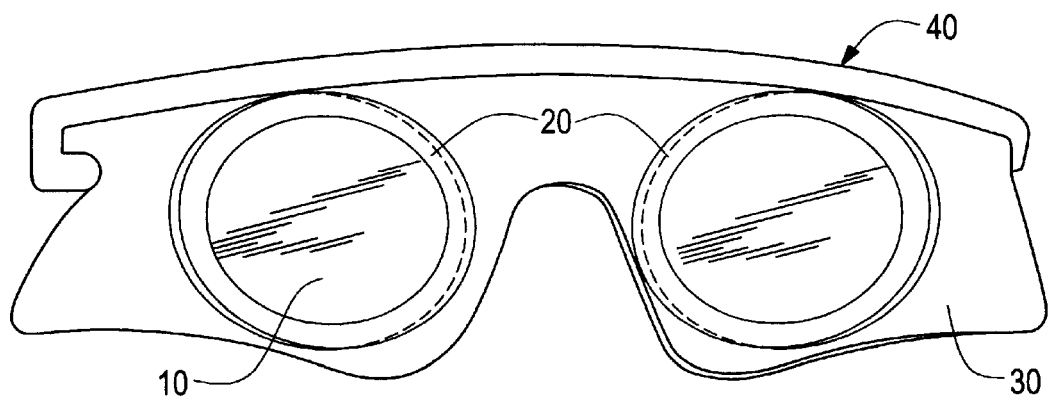
Figure 3A:
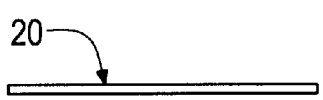
Figure 3B:
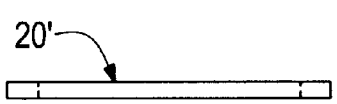
Figure 3C:
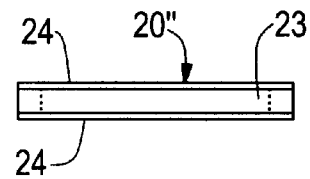
Figure 4A:
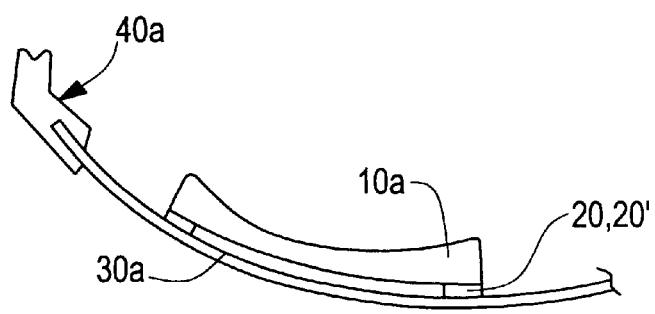
Figure 4B:
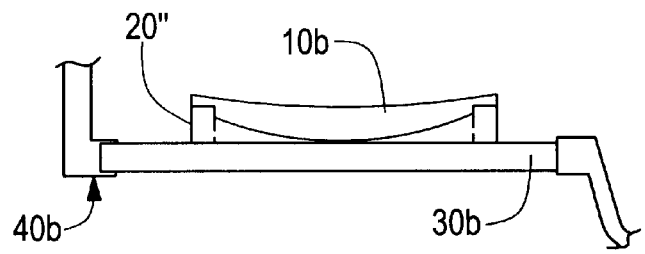
Figure 5A:
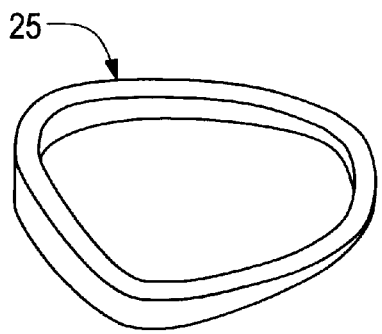
Figure 5B:

In the following embodiments, the present invention is explained in detail by means of the attached drawings. Shown are:

FIG. 1, a perspective representation of the individual components of the system consisting of a shield of a pair of safety glasses, an embodiment of the adapter according to the invention and the spectacle lens;

FIG. 2a, the system of FIG. 1, in which the individual components are interconnected;

FIG. 2b, an optical section through the system of FIG. 2;

FIGS. 3a through 3c, lateral views of various embodiments of the adapter according to the invention;

FIG. 4a, a section through the curved flat shield of a pair of diver's goggles with a concave spectacle lens;

FIG. 4b, a section through the flat shield of a pair of diver's goggles with a convex spectacle lens;

FIG. 5a, a perspective of a cross-section of the wedge-shaped adapter;

FIG. 5b, a cross-section through the adapter of FIG. 5a.

FIGS. 1 through 2b show a system 1 consisting of a spectacle lens 10, an adapter according to the invention 20 in the form of a shaped ring, and a shield 30 of a pair of safety goggles 40 or, for example, a pair of sports glasses, diver's goggles or safety glasses. The spectacle lens 10 is connected at the front to an adapter 20, whose lateral surfaces 21, 22 consist of an adhesive material. The unit comprising the spectacle lens 10 and the adapter 20 is connected from the rear to the shield 30. The adhesive joint is fixed and immovable, but removable.

This is advantageous if the shield 30 is of a high optical and mechanical quality, and possibly has a rotation-symmetrical fundamental curve or base curve. Shields used in most commercial safety glasses meet these requirements. Shields which only consist of a curved sheet are not suitable. The spectacle lens 10 should preferably have the same curvature or base curve as the shield 30. According to specific details such as spacing of the eyes, corneal vertex distance, cutting height, lens thicknesses, in particular, with respect to very thick lenses and oblique astigmatism, the user should convert the thickness of the spectacle lenses in order to keep the astigmatism of oblique bundles which can be expected with curved shields 30 and when the spectacle lenses 10 are no longer in vertical position, within non-interfering limits. This conversion is part of the expert knowledge of opticians and, therefore, does not require detailed explanation (compare Pforte, Der Feinoptiker [The High-Precision Optician], Part II).

Practically all types of single or multifocal spectacle lenses can be processed if the respective fundamental optical requirements are taken into consideration.

FIGS. 3a–3c show various embodiments of an adapter 20, 20', 20". The adapters 20, 20' shown in FIG. 3a and 3b are self-adhesive strips of 0.5 mm or 2 mm thickness of a permanently elastic transparent or opaque material. Also suitable are adhesive strips produced by the company 3M with the designation VHB 4905 P, 4910 F, 4912 F, 4915 F, 4918 F. The adapter 20" shown in FIG. 3c has a core 23 made of a plastic material such as nylon or polycarbonate, which is approximately 3.5 mm thick and lined on both sides with a self-adhesive layer 24, which is about 0.5 mm thick.

FIGS. 4a and 4b show sections through a concave or convex spectacle lens 10a, 10bb, which is fixed on a curved shield 30a of a pair of sports glasses 40a, or a flat shield 30b of a pair of diver's goggles 40b. FIG. 4a shows that the curved shield 30a and the front of the spectacle lens 10a have the same curvature or basic curve, so that a flat adapter 20, 20' can be used. By contrast, the front of the convex spectacle lens 10b in FIG. 4b has a strong curvature, whereas the shield 30b of the pair of diver's goggles 40b is flat. This is balanced by using a stronger adapter 20".

FIGS. 5a and 5b show another adapter 25, which has a wedge-shaped cross section. The wedge-shaped cross section also allows the balancing of the different curvatures of the shield 30 and the front of the spectacle lens 10.

What is claimed is:

1. Adapter (20) for reversibly fixing a spectacle lens (10) to a shield (30) of a pair of safety glasses (40), said adapter (20) comprising a shaped ring with a flat cross section, said shaped ring comprising permanently elastic material, in which said shaped ring has adhesive surfaces for joining a spectacle lens (10) to a shield (30).

2. Adapter as defined in claim 1, characterized by the fact that the shaped ring comprises an adhesive tape.

3. Adapter as defined in claim 2 wherein said adhesive tape has a thickness between 0.5 mm and 2.0 mm.

4. Adapter (20) for reversibly fixing a spectacle lens (10) to a shield (30) of a pair of safety glasses (40), said adapter (20) comprising a shaped ring with a wedge-shaped cross section, said shaped ring comprising a permanently elastic material, in which said shaped ring has adhesive surfaces for joining a spectacle lens (10) to a shield (30).

5. Adapter (20) for reversibly fixing a spectacle lens (10) to a shield (30) of a pair of safety glasses (40), said adapter (20) comprising a shaped ring with a flat cross-section, said shaped ring comprising a permanently elastic material, in which said shaped ring has adhesive surfaces for joining a spectacle lens (10) to a shield (30), characterized by the fact that the shaped ring has a core (23) of a transparent material which has adhesive surfaces in the form of at least one layer (24) of an adhesive material.

6. Adapter as defined in claim 5, characterized by the fact that the core consists of a plastic material.

7. Adapter as defined in claim 6 wherein said plastic material is selected from the group consisting of polycarbonate and nylon.

8. System (1) comprising a pair of safety glasses (40) with at least one shield (30) and spectacle lenses (10) reversibly fixed thereon, characterized by the fact that the spectacle lenses (10) are attached to the shield by means of an adapter (20) according to any one of claims 1, 2–7 or 10–14.

9. System as defined in claim 1, in which the safety glasses are selected from the group consisting of sports glasses, sport sunglasses, diver's goggles, and industrial safety glasses.

10. Adapter (20) for reversibly fixing a spectacle lens (10) to a shield (30) of a pair of safety glasses (40), said adapter (20) comprising a shaped ring with a flat cross section, said shaped ring comprising a permanently elastic material, in which said shaped ring has adhesive surfaces for joining a spectacle lens (10) to a shield (30), wherein said permanently elastic material is transparent.

11. Adapter (20) for reversibly fixing a spectacle lens (10) to a shield (30) of a pair of safety glasses (40), said adapter (20) comprising a shaped ring with a flat cross section, said shaped ring comprising a permanently elastic material, in which said shaped ring has adhesive surfaces for joining a spectacle lens (10) to a shield (30), wherein said permanently elastic material is opaque.

12. Adapter (20) for reversibly fixing a spectacle lens (10) to a shield (30) of a pair of safety glasses (40), said adapter (20) comprising a shaped ring with a flat cross section, said shaped ring comprising a permanently elastic material, in which said shaped ring has adhesive surfaces for joining a spectacle lens (10) to a shield (30), characterized by the fact that the shaped ring has a core (23) of an opaque material which has adhesive surfaces in the form of at least one layer (24) of an adhesive material.

13. Adapter as defined in claim 12, characterized by the fact that the core consists of a plastic material.

14. Adapter as defined in claim 13 wherein said plastic material is selected from the group consisting of polycarbonate and nylon.

15. System (1) comprising a pair of safety glasses (40) with at least one shield (30) and spectacle lenses (10) reversibly fixed thereon, characterized by the fact that the spectacle lenses (10) are attached to the shield by means of an adapter (20) according to any one of claims 1, 2–7 or 10–14 and wherein said at least one shield is transparent and wherein said spectacle lenses are circular.

* * * * *